United States Patent [19]

Kleemiss

[11] Patent Number: 5,659,081
[45] Date of Patent: Aug. 19, 1997

[54] PROCESS FOR THE PREPARATION OF CYCLOPROPANECARBOXAMIDE

[75] Inventor: Wolfgang Kleemiss, Haltern, Germany

[73] Assignee: Huels Aktiengesellschaft, Marl, Germany

[21] Appl. No.: 669,832

[22] Filed: Jun. 26, 1996

Related U.S. Application Data

[63] Continuation of Ser. No. 350,028, Nov. 29, 1994, abandoned.

[30] Foreign Application Priority Data

Jan. 7, 1994 [DE] Germany ............... 44 00 328.5

[51] Int. Cl.⁶ ........................................ C07C 231/02
[52] U.S. Cl. ........................................ 564/134
[58] Field of Search ........................................ 564/134

[56] References Cited

U.S. PATENT DOCUMENTS

| | | |
|---|---|---|
| 4,379,928 | 4/1983 | Theodoropulos ............ 544/176 |
| 4,590,292 | 5/1986 | Blackwell et al. ............ 560/124 |
| 5,068,428 | 11/1991 | Diehl et al. ............ 564/134 |

FOREIGN PATENT DOCUMENTS

| | | |
|---|---|---|
| 0 043 949 | 1/1982 | European Pat. Off. . |
| 0 205 403 | 12/1986 | European Pat. Off. . |
| 0 365 970 | 5/1990 | European Pat. Off. . |
| 2.093.472 | 1/1972 | France . |
| 1 939 759 | 3/1970 | Germany . |

*Primary Examiner*—Shailendra Kumar
*Attorney, Agent, or Firm*—Oblon, Spivak, McClelland, Maier & Neustadt, P.C.

[57] ABSTRACT

In a process for the preparation of cyclopropanecarboxamide by amidating cyclopropanecarboxylic esters with ammonia in alcoholic solution at from 60° to 200° C., the reaction being catalyzed by an alcoholate of a monohydric alcohol, high yields are achieved even in the absence of a hydrocarbon solvent when a cyclopropanecarboxylic ester of the formula

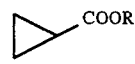

in which R is $C_1$- to $C_3$-alkyl or cyclopropyl, is employed.

12 Claims, No Drawings

PROCESS FOR THE PREPARATION OF CYCLOPROPANECARBOXAMIDE

This application is a Continuation of application Ser. No. 08/350,028, filed on Nov. 29, 1994, now abandoned.

BACKGROUND OF THE INVENTION

The present invention relates to a new process for the preparation of cyclopropanecarboxamide by amidation of a cyclopropanecarboxylic ester with ammonia, in a monohydric alcohol of 1 to 8 carbon atoms as solvent, the reaction being catalyzed by an alcoholate of 1 to 8 carbon atoms and carried out at from 60° to 200° C.

FIELD OF THE INVENTION

Cyclopropanecarboxamide is an important fine chemical. Its great importance is exemplified by its conversion to cyclopropylamine, which is employed in the pharmaceutical and plant protection industries. It is therefore necessary to have processes for the preparation of cyclopropanecarboxamide which ensure a combination of high product purity and high yield.

The preparation of cyclopropanecarboxamide by amidation of cyclopropanecarboxylic esters is known. For instance, in U.S. Pat. No. 3,711,549, methyl cyclopropanecarboxylate is reacted with ammonia at 80° C. using 15 mol % of a 10 to 17% strength solution of sodium methylate in methanol as catalyst, the addition of toluene being necessary in order to obtain good yields of amide (conversion: about 90%). The reaction time here is about 4 hours. According to U.S. Pat. No. 3,711,549, toluene is necessary in order to shift the equilibrium in the direction of the amide. The work-up procedure described in this patent is highly complex. After the reaction, unreacted methyl cyclopropanecarboxylate, toluene and methanol are distilled off. The sodium methylate which remains in the bottom of the distillation column is neutralized using dilute hydrochloric acid, and in this way the amide is taken up in water. Therefore, the resulting solution is not only highly dilute but also contains sodium chloride.

EP-A-0 205 403 indicates that the amidation of esters of cyclopropanecarboxylic acid with sterically hindered, secondary or tertiary alcohols is achieved with good yields when a sodium salt of a polyhydric alcohol such as ethylene glycol or glycerol is used as basic catalyst. In this case the catalyst is prepared by dissolving sodium hydroxide in an excess of the polyhydric alcohol and stripping off the water of reaction in vacuo. 20 mol % of sodium glycolate are preferably used for the amidation. In order to obtain a homogenized reaction mixture, a large excess of glycol or of a hydrocarbon solvent such as, for example, xylene is used. The reaction of cyclopropanecarboxylic esters in this medium at a temperature of about 100° C. under an ammonia pressure of from 3 to 6 bar leads after about 3 hours to a conversion of >99%. However, the work-up procedure for the amide is complex. The reaction mixture must be cooled to 0° C. to crystallize sufficient product. Subsequently, the product isolated by filtration is washed with butanol. After removal of the butanol by distillation, the mother liquor can be employed for a further amidation. After five reaction cycles an average amide yield of 92% is obtained. This process, however, has the disadvantage that at least 2 different solvents are used and, in addition, the preparation of catalyst is very laborious.

A further simplification of the preparation is described in EP-A-0 365 970. In this case, cyclopropanecarboxylic esters of the formula

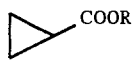

in which R is straight-chain or branched $C_4$ to $C_8$ alkyl, are reacted in the presence of an alkali metal alcoholate of a monohydric $C_1$ to $C_8$ alcohol. The yields of cyclopropanecarboxamide obtained are very good, the patent referring to the fact that no additional hydrocarbon solvent is necessary. The product is obtained after the reaction by filtration. Furthermore, after excess butanol as been separated off by distillation, the mother liquor an be employed for a plurality of reactions. The yield of amide is then virtually quantitative.

In this process the ester conversion is >99%, and the reaction mixture from which the amide crystallizes out remains stirrable and is capable of being readily filtered. The butanol which is liberated in the reaction is used to obtain a manageable reaction mixture which is nevertheless sufficiently concentrated for filtration at room temperature to yield sufficient product.

However, this process is limited to the use of cyclopropanecarboxylic esters of higher alcohols ($C_4$ to $C_8$), since it is only when these esters are used that the alcohol formed during amidation ensures that the reaction mixture, even after 99% conversion, remains stirrable and capable of being readily filtered at room temperature.

When esters of lower alcohols ($C_1$ to $C_3$) are used, the result after complete ester conversion using identical concentrations of alcoholate is a solid reaction mixture which can no longer be filtered. If, however, a more dilute solution of alcoholate is employed, the rate of reaction for the amidation falls dramatically.

SUMMARY OF THE INVENTION

It is therefore an object of the present invention to prepare cyclopropanecarboxamide in high yields by amidating one or more short-chain alcohol esters of cyclopropanecarboxylic acid under mild conditions and without using additional hydrocarbon solvent(s).

It is a further object of the present invention to prepare cyclopropanecarboxamide using a simple catalyst which is preferably commercially available.

Therefore, in accordance with the present invention, these and other objects are achieved by amidating one or more cyclopropanecarboxylic esters of the formula

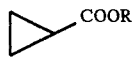

in which R is $C_1$- to $C_3$-alkyl or cyclopropyl, with ammonia in an alcoholic solution at a temperature of from 60° to 200° C., catalyzed by an alcoholate of a monohydric alcohol of 1 to 8 carbon atoms.

DETAILED DESCRIPTION OF THE PREFERRED EMBODIMENTS

If the amidation is carried out up to a conversion of >99%, the result is a reaction mixture which is solid at room temperature and which is difficult to handle during work-up. Preferably, therefore, amidation is conducted to a conversion of from 60 to 90%. Thereafter, the process may comprise separating precipitated or crystallized cyclopropanecarboxamide, and feeding the remaining mother liquor to a second reaction vessel for a further amidation reaction.

By virtue of these measures, it is possible to prepare cyclopropanecarboxamide in high yields (i.e., in yields of more than 80%, preferably more than 90%) even without the addition of a hydrocarbon solvent such as toluene, in contrast to the indications of U.S. Pat. No. 3,711,549.

An essential aspect of one preferred embodiment of the present invention is that the amidating step is only carried out up to an ester conversion of from 60 to 90%, preferably from 70 to 85%. The resulting reaction mixture is then still stirrable even at room temperature. The mixture can be filtered or centrifuged without problems. The mother liquor, containing not only alcoholate but also unreacted ester, may be employed for a new amidation, after replenishing the ester if desired.

Examples of suitable $C_1$-$C_3$ esters of cyclopropanecarboxylic acid are the methyl, ethyl, propyl and isopropyl esters. The methyl and ethyl esters of cyclopropanecarboxylic acid are preferred, since the corresponding alcohols—methanol and ethanol—which are then formed in accordance with the reaction can be distilled off at relatively low temperatures.

Suitable catalysts are alcoholates of magnesium, calcium, barium and in particular of alkali metals. In this context the alcoholates of the alkali metals lithium, sodium, potassium, rubidium or caesium can be employed, preference being given to sodium alcoholates and potassium alcoholates.

The alcoholates used may be those of, for example, methanol, ethanol, propanol, isopropanol, n-butanol, t-butanol, hexanol, heptanol or octanol. Preferably, however, alcoholates of $C_1$ to $C_4$ alcohols are employed, with very particular preference being given to an alkali metal methylate. In general, the alcohol employed as a solvent and the alcohol from which the alcoholate derives have the same number of carbon atoms.

The alcoholate is preferably employed in a quantity of from 2 to 40 mol %, in particular from 10 to 30 mol %, based on the number of mols of the cyclopropanecarboxylic ester.

Owing to the ready solubility of ammonia in alcohol, amidation can be carried out at a comparatively low ammonia pressure. The amidation is preferably carried out at an ammonia pressure of from 1 to 6 bar, particularly preferably from 1 to 3 bar. A particular characteristic of the present process is that the amidation can even be carried out at an ammonia pressure of 1 bar, giving the amide in high yields.

The amidation is preferably performed at from 60° to 150° C., with temperatures of from 60° to 100° C. being very particularly preferred.

When the cyclopropanecarboxamide is separated off in the form of crystals, which is generally carried out by filtration or centrifugation at from 0° to 25° C., the conditions are preferably chosen such that the saturation concentration of the alcoholate in the mixture is not exceeded. In this way, virtually the entire quantity of alcoholate can be reused for a further amidation. For this second amidation, it is preferred to add additional cyclopropanecarboxylic ester of the formula above. Preferably, an amount of the cyclopropanecarboxylic ester from 60 to 90% by weight of the amount in the first amidating step is added prior to the second amidating step.

A significant advantage of the present process is that the amidation can be carried out without an additional solvent, for example toluene, xylene, ethylene glycol or glycerol, while it is nevertheless possible to use the cyclopropanecarboxylic esters of lower alcohols. Furthermore, cyclopropanecarboxylic esters of lower alcohols ($C_1$ to $C_3$) are easy to prepare, for example in accordance with DE-A-42 22 497.

The use of these esters also increases the space-time yield of the amidation. In this context, the highest space-time yields are achieved when the starting product used is the methyl or ethyl ester of cyclopropanecarboxylic acid. The choice of esters of lower alcohols makes it possible to distill off the alcohol formed during the amidation in a simple manner at low temperature.

In the practical implementation of the present process, the general procedure is to add the alcoholate, in the form of a 10 to 40% strength solution in the corresponding alcohol, to the cyclopropanecarboxylic ester. After addition of ammonia, the reaction mixture is heated to the reaction temperature in an autoclave.

After the reaction, the product is filtered off and washed with alcohol. The mother liquor is then concentrated and, after optionally adding more ester, the mother liquor can be used for a subsequent amidation. Based on the conversion of the ester, the yield of amide over a plurality of reaction cycles is virtually quantitative.

Optionally, the reaction mixture can be cooled for 2 hours to 0° to 5° C. after the amidation reaction. Cyclopropanecarboxamide is then filtered off and washed with alcohol. The mother liquor is concentrated, and can likewise again be employed for a further amidation of cyclopropanecarboxylic ester: In this case, the yield of amide obtained, based on the ester, is also virtually quantitative if the reaction is carried out over a plurality of cycles.

Other features of the present invention will become apparent in the course of the following descriptions of exemplary embodiments which are given for illustration of the invention, and are not intended to be limiting thereof. Therefore, the following examples are intended to illustrate the invention without limiting the invention in any manner.

COMPARATIVE EXAMPLE 1

(complete ester conversion without reusing the mother liquor)

500 g (5 mol) of methyl cyclopropanecarboxylate and 90 g (0.5 mol) of 30% strength sodium methylate solution are placed in a 5 l stirred autoclave, and the mixture is heated to 70° C. Ammonia is injected up to a pressure of 5 bar. The temperature rises to 80° C. over the course of 2 minutes. The reaction is allowed to continue for 5 hours at 80° C. under an ammonia pressure of from 5 to 5.5 bar. The reaction mixture is then cooled, and no further ammonia is injected, the pressure falling to about 2 bar. The solid contents of the reactor are taken up in 500 g of methanol. An ester conversion of >99% is determined by GC analysis. The solution is concentrated to dryness in a distillation flask. The residue is recrystallized from hot methanol and the product is washed with cold methanol (312 g, purity: 99.5%, yield: 73%). The mother liquor (480 g) is then concentrated to 182 g and cooled to 5° C. The precipitated amide is filtered off and washed with cold methanol (49 g, purity: 99.5%, yield: 11.5%).

Total yield: 84.5%.

COMPARATIVE EXAMPLE 2

(complete ester conversion without reusing the mother liquor)

The amidation is carried out as in Example 1 (ester conversion: >99%). The solid contents of the reactor are removed from the autoclave using 500 g of methanol. 242 g of 20% strength hydrochloric acid are added to this solution to adjust the pH to 7. The mixture is concentrated to dryness, and the residue is taken up in methanol.

Solid sodium chloride is removed by filtration. The solution is again concentrated to dryness. The residue is taken up in methanol again, and residues of sodium chloride are removed by filtration. The methanolic solution is then concentrated to 400 g and cooled to 5° C. The precipitated amide is filtered off and washed with cold methanol (345 purity: 99.5%, yield: 81%). The mother liquor is then concentrated to 100 g and cooled to 5° C. The precipitated amide is filtered off and washed with a little cold methanol (55 g, GC purity: 99.5%, yield: 13%).

Overall yield: 94%.

EXAMPLE 1

(incomplete ester conversion with reuse of the mother liquor)

700.7 g (7 mol) of methyl cyclopropanecarboxylate and 252.7 g (1.4 mol) of 30% strength sodium methylate solution are placed in a 2 l four-necked flask, and the mixture is heated to 60° C. Ammonia is passed into the mixture with stirring. Subsequently, ammonia is added continuously in a quantity such as to give an excess pressure of from about 1.1 to 1.3 bar. The mixture is stirred at 60° C. for 14 hours. After this time, the conversion of ester is 71%.

The reaction mixture is cooled to 5° C. and, after 2 hours, the amide is filtered off. The product is washed with cold methanol and dried (280 g; 3.3 mol; 47%). A portion of the methanol (200 g) is removed from the mother liquor by distillation. The proportion of ester reacted in the first batch is added to the remaining mother liquor (480 g; 4.89 mol).

The mixture is heated to 60° C. and ammonia is passed in for 12.5 hours (conversion of ester: 81%). The mixture is then cooled to 5° C. The precipitated amide is filtered off, washed with methanol and dried (450 g; 5.3 mol; 93%). The mother liquor is again concentrated (the quantity of methanol distilled off: 200 g). The results of two further reaction cycles are as follows: ester conversion: 79% and 70%; yield, based on conversion: 85% and 90%.

EXAMPLE 2

(incomplete ester conversion with reuse of the mother liquor)

700.7 g (7 mol) of methyl cyclopropanecarboxylate and 252.7 g (1.4 mol) of 30% strength sodium methylate solution are placed in a 2 l four-necked flask, and the mixture is heated to 60° C. Ammonia is passed into the mixture with stirring. Subsequently, ammonia is added permanently in a quantity such as to give an excess pressure of from 1.1 to 1.3 bar. The mixture is stirred at 60° C. for 14 hours. After this time, the conversion of ester is about 70%. The methanol which is formed during the amidation (157 g) is then removed by distillation. During this procedure, because of the ammonia which is still in solution, the conversion rises to about 80%. The reaction mixture is cooled to room temperature, and the crystallized product is filtered off and washed with 100 g of cold methanol (0° to 5° C). Yield: 287 g (3.37 mol; 60% based on the conversion).

560 g (5.6 mol) of methyl cyclopropanecarboxylate are added to the mother liquor, and the reaction is started anew. The reaction is again carried out up to a conversion of 70%, and the methanol formed in the reaction is then removed by distillation (157 g), resulting in an ester conversion of 80%. The amide yield is then 423 g (4.97 mol; 89% based on the ester conversion).

Obviously, numerous modifications and variations of the present invention are possible in light of the above teachings. It is therefore to be understood that within the scope of the appended claims, the invention may be practiced otherwise than as specifically described herein.

What is claimed:

1. A process for the preparation of cyclopropanecarboxamide, comprising amidating a cyclopropanecarboxylic ester of the formula

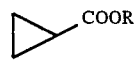

in which R is $C_1$- to $C_3$-alkyl or cyclopropyl, with ammonia in an alcohol solvent, in the presence of a catalyst comprising an alcoholate of a monohydric alcohol of 1 to 8 carbon atoms, at a temperature of from 60° to 200° C., in the absence of a hydrocarbon solvent, wherein said amidating is carried out to a conversion of from 60 to 90%, and said process further comprises separating solid cyclopropanecarboxamide to provide a mother liquor, and transferring said mother liquor to a reaction vessel for a further amidation.

2. The process according to claim 1, wherein said cyclopropanecarboxylic ester is methyl cyclopropanecarboxylate or ethyl cyclopropanecarboxylate.

3. The process according to claim 1, wherein said catalyst is an alkali metal alcoholate.

4. The process according to claim 1, wherein said alcohol solvent has from 1 to 4 carbon atoms.

5. The process according to claim 1, wherein said catalyst comprises from 2 to 40, mol % of said alcoholate, based on the number of mols of the cyclopropanecarboxylic ester.

6. The process according to claim 1, wherein said amidatingg is carried out under an ammonia pressure of from 1 to 6 bar.

7. The process according to claim 6, wherein said ammonia pressure is from 1 to 3 bar.

8. The process according to claim 1, wherein said amidating is carried out at a temperature of from 60° to 150° C.

9. The process according to claim 8, wherein said temperature is from 60° to 100° C.

10. The process according to claim 1, wherein said conversion is from 70 to 85%.

11. The process according to claim 1, wherein said solid cyclopropanecarboxamide is in the form of crystals, and said alcoholate in said amidating step does not exceed a saturation concentration.

12. The process according to claim 1, further comprising the steps of adding additional cyclopropanecarboxylic ester to said mother liquor and amidating said additional cyclopropanecarboxylic ester in said mother liquor.

* * * * *